(12) United States Patent
Grimm

(10) Patent No.: US 12,239,354 B2
(45) Date of Patent: *Mar. 4, 2025

(54) CRYOSURGICAL PROBE WITH ENHANCED THERMAL PERFORMANCE

(71) Applicant: Varian Medical Systems, Inc., Palo Alto, CA (US)

(72) Inventor: Daniel N. Grimm, Round Rock, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,647

(22) Filed: Aug. 9, 2023

(65) Prior Publication Data

US 2024/0016532 A1     Jan. 18, 2024

Related U.S. Application Data

(63) Continuation of application No. 16/919,995, filed on Jul. 2, 2020, now Pat. No. 11,723,707.

(51) Int. Cl.
*A61B 18/02*     (2006.01)
*A61B 18/00*     (2006.01)

(52) U.S. Cl.
CPC .... *A61B 18/02* (2013.01); *A61B 2018/00035* (2013.01); *A61B 2018/0262* (2013.01)

(58) Field of Classification Search
CPC .......... A61B 18/02; A61B 2018/00035; A61B 2018/0262
See application file for complete search history.

(56) References Cited

U.S. PATENT DOCUMENTS

| 5,520,682 A | 5/1996 | Baust et al. |
| 5,992,158 A | 11/1999 | Goddard et al. |
| 6,270,493 B1 | 8/2001 | Lalonde et al. |

(Continued)

FOREIGN PATENT DOCUMENTS

| GB | 1570401 A | 7/1980 |
| WO | 2011119279 A2 | 9/2011 |

OTHER PUBLICATIONS

Extended European Search Report for European Patent Application No. 21182952.8 issued Nov. 22, 2021.

(Continued)

*Primary Examiner* — Linda C Dvorak
*Assistant Examiner* — Abigail Bock
(74) *Attorney, Agent, or Firm* — Duane Morris LLP

(57) ABSTRACT

A probe and method of using a probe are disclosed. The probe may comprise a first member, a tip, a second member, and a third member. The first member may have a first and second end portions. The tip may be configured to engaged to the first member at the second end portion. The second member may be configured to extend and be positioned within the first member. The third member may be configured to be disposed outward of the second member along at least a portion of the second member, engage an inner surface of the first member, and define to least one passage between the third member and the first member. The probe may be coupled to a fluid supply and return, and fluid may flow within the probe, including within the passage defined between the first and third members.

20 Claims, 16 Drawing Sheets

(56) References Cited

U.S. PATENT DOCUMENTS

| | | |
|---|---|---|
| 7,410,484 B2 | 8/2008 | Littrup et al. |
| 7,967,815 B1 | 6/2011 | Berzak et al. |
| 8,083,733 B2 | 12/2011 | Toubia et al. |
| 8,597,285 B2 | 12/2013 | Delonzor et al. |
| 9,050,072 B2 | 6/2015 | Delonzor et al. |
| 9,050,075 B2 | 6/2015 | Berzak et al. |
| 9,408,656 B2 | 8/2016 | Littrup et al. |
| 9,554,842 B2 | 1/2017 | Delonzor et al. |
| 11,723,707 B2 * | 8/2023 | Grimm ................. A61B 18/02 606/23 |
| 2007/0149959 A1 | 6/2007 | DeLonzor et al. |
| 2009/0000571 A1 | 1/2009 | Alvarado Barrientos |
| 2011/0178514 A1 | 7/2011 | Levin et al. |
| 2012/0232543 A1 | 9/2012 | Sharon et al. |
| 2020/0085485 A1 | 3/2020 | Skorich et al. |

OTHER PUBLICATIONS

Office Action issued for European Patent Application No. 21182952.8 dated Oct. 8, 2024, 10 pages.

\* cited by examiner

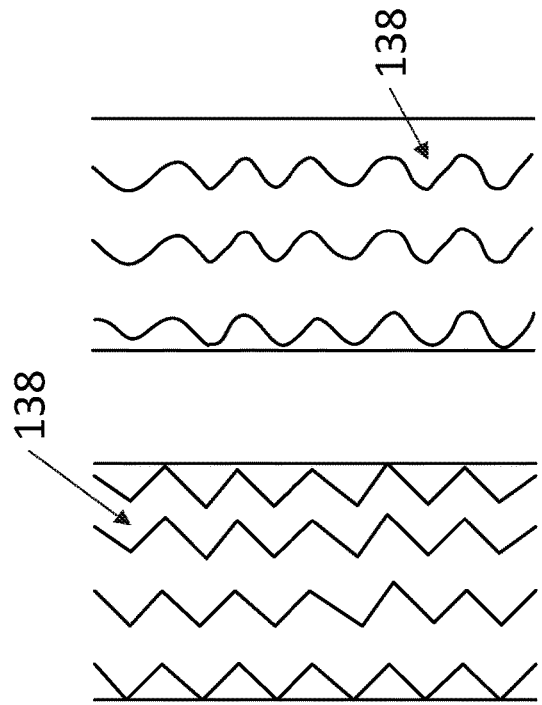
FIG. 6B
FIG. 6C
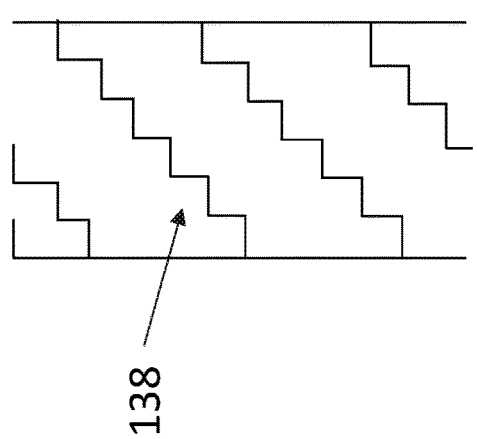
FIG. 6A
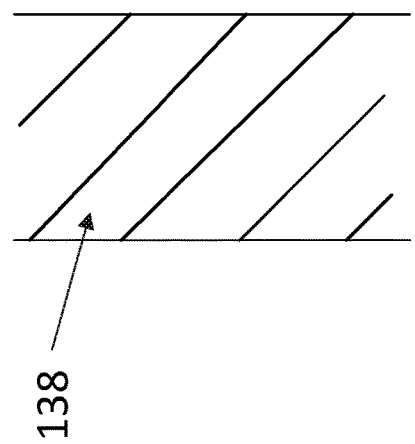
FIG. 6D

CRYOSURGICAL PROBE WITH ENHANCED THERMAL PERFORMANCE

RELATED APPLICATIONS

This application is a continuation of U.S. patent application Ser. No. 16/919,995 filed on Jul. 2, 2020 now issued as U.S. Pat. No. 11,723,707. The entire disclosure of the above application is incorporated herein by reference.

TECHNICAL FIELD

The disclosure relates generally to medical instruments and, more specifically, to cryosurgical probes and methods of using the same.

BACKGROUND

Cryosurgical probes are instruments used in medical procedures. One such procedure is cryoablation. During cryoablation, an extremely cold fluid (liquid, gas, mixed, or other phase) may be passed through a probe in thermal contact with a target tissue. Heat from the tissue passes from the tissue, through the probe, and into the fluid that removes heat from the targeted tissue. This removal of heat causes tissue to freeze, resulting in the destruction of the targeted tissue. The thermal performance of the probe depends on the rate at which it can remove heat from the tissue.

SUMMARY

The embodiments described herein are directed to cryosurgical probes that have improved thermal performance over existing designs. The improved performance of the embodiments described herein can result in shorter times to cool and freeze tissues, freeze larger volumes of tissues, or both. Increased thermal performance also results in using less fluid for a given procedure, resulting in both cost savings and lowering the outlet mass flowrate of the fluid.

In accordance with some embodiments, a probe and method of using a probe are disclosed. The probe may comprise a first member, a tip, a second member, and a third member. The first member may have a first and second end portions. The tip may be configured to engaged to the first member at the second end portion. The second member may be configured to extend and be positioned within the first member. The third member may be configured to be disposed outward of the second member along at least a portion of the second member, engage an inner surface of the first member, and define to least one passage between the third member and the first member. The probe may be coupled to a fluid supply and return, and fluid may flow within the probe, including within the passage defined between the first and third members.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein:

FIGS. 6A-6D illustrate various channel designs in accordance with some embodiments;

DETAILED DESCRIPTION

Figure 1:
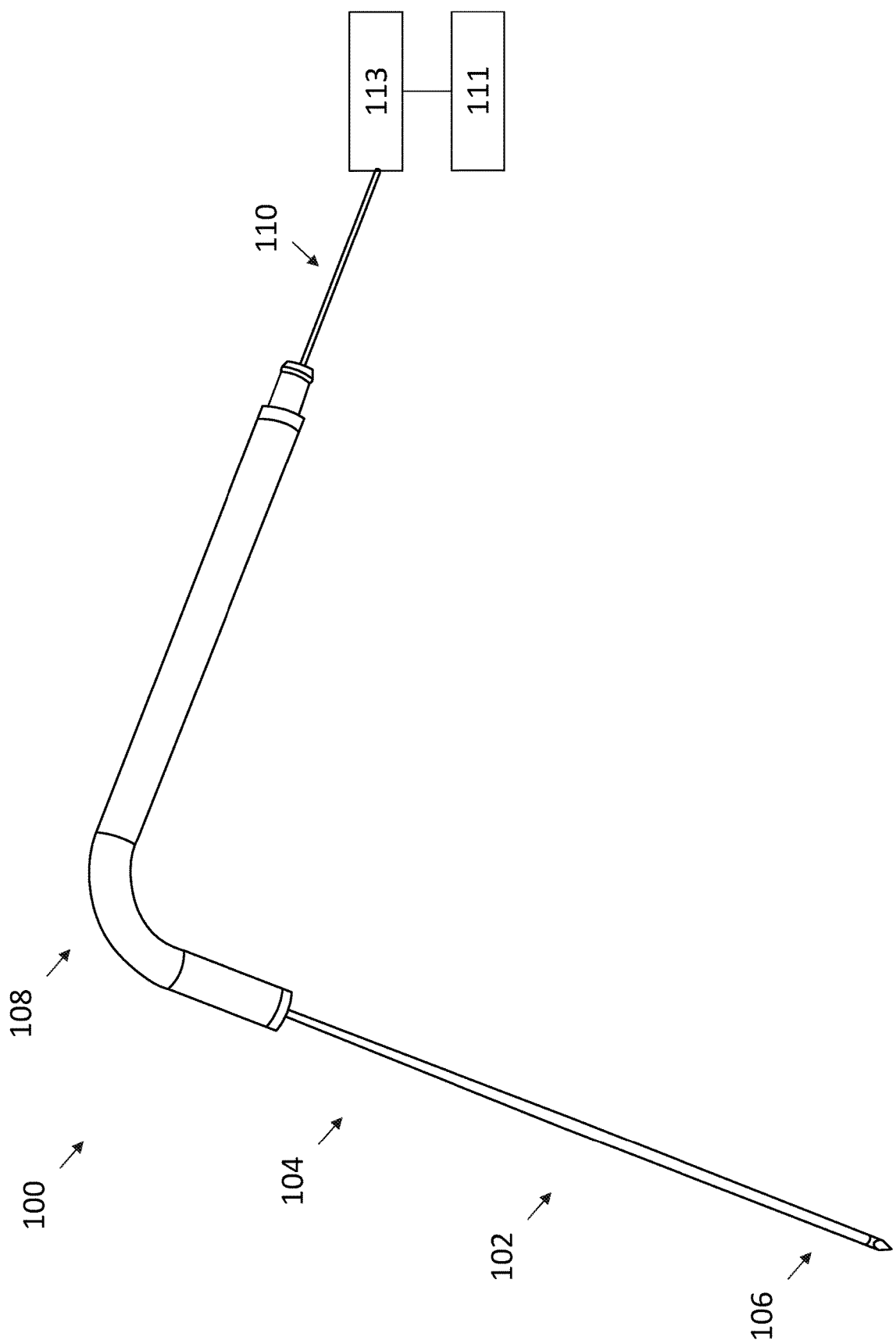
FIG. 1 is a perspective view of a probe in accordance with some embodiments.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

FIG. 1 illustrates perspective view of a probe 100 in accordance with some embodiments presented herein. Probe 100 may have a first member 102 that has a first end portion 104 and a second end portion 106. First member 102 may have elongated, hollow structure extending from the first end portion 104 to the second end portion 106. This structure may be tubular, having a generally circular inner and outer diameters, and may have a generally constant inner and outer dimensions (e.g., radii) between the first end portion 104 and second end portion 106. The first end portion 104 is coupled to a handle 108. The first end portion 104 may be referred to as the proximal end of the first member 102 because of this connection to the handle 108. Likewise, second end portion 106 may be referred to the distal end of the first member 102 because it is more distant from the handle 108 as well as other equipment (e.g., a fluid supply, a fluid return, electrical connections for temperature sensors, etc.).

The first member 102 may comprise various materials including stainless steel, Inconel, titanium, or other materials.

Handle 108 serves two primary functions. First, the handle 108 improves a surgeon's ability to physically manipulate the probe location and orientation. Second, the handle 108 may provide physical connections between the inlet and outlet fluid flow paths within the first member 102 and a fluid supply and a fluid return, respectively, as well as for any electrical connections between components of the first member 102 and support equipment. These connections may be physically grouped together in a bundle 110 that may be operably coupled to cryogen source 111 (which may include a fluid return, or the return may be separated therefrom), console 113 (cryogen source 111 may be integrated with console 113).

Fluids utilized by probe 100 may include, but are not limited to, argon, gaseous nitrogen, helium, refrigerants, liquid nitrogen, and other fluids.

Figure 2:
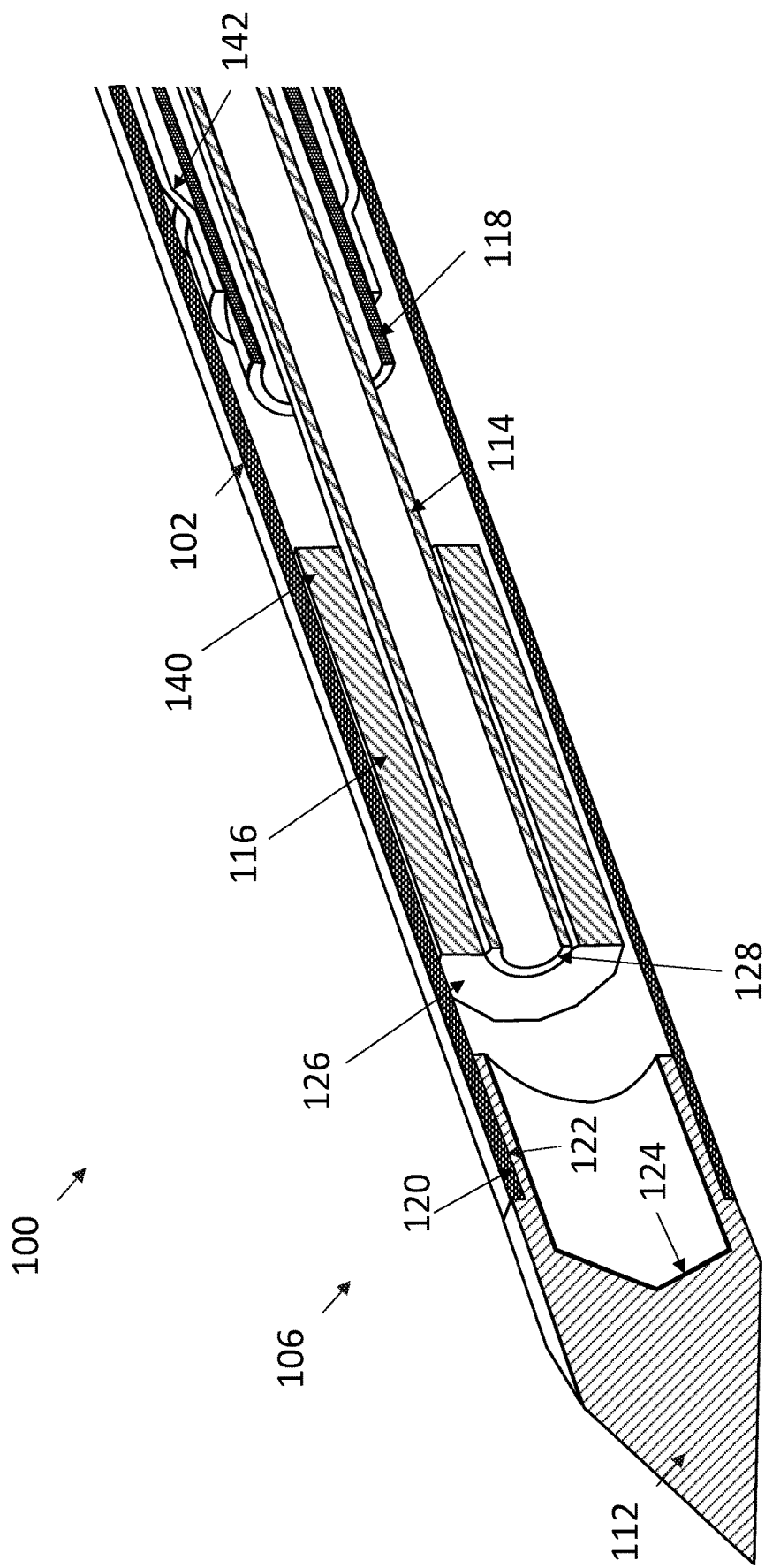
FIG. 2 is a perspective, cutaway view of an end of a probe in accordance with some embodiments.

FIG. 2 is a perspective, cutaway view of the second end portion 106 of a probe 100 in accordance with some embodiments. The first member 102 is coupled to a tip 112 at the extreme distal end of probe 100. Tip 112 may be rounded, or it may be sharpened to aid movement of the probe through tissue. Tip 112 may have a surface 120 that engages a surface 122 of the first member 102. Once engaged, the tip 112 may be secured to the first member 102. As shown in FIG. 2, the surface 120 of tip 112 may be located on a flange that engages an inner surface 122 of the first member 102, although other arrangements may be made. The Tip 112 may have an inner surface 124 that this conical, as shown in FIG. 2, flat, rounded, or hollow.

Also shown in FIG. 2 is the second member 114. Second member 114 may provide at least part of the pathway for fluid from the fluid supply to the probe tip 112. The second member 114 may be positioned within first member 102 such that the second member 114 extends within the first member 102. This extension may be adjacent to the second end portion 106 of probe 100. This extension may be along a longitudinal axis of the first member 102, around which the second member 114 may be centered. However, all embodiments are not so limited, and in some embodiments the second member 114 may extend generally along the longitudinal axis of the first member 102 but be displaced from the longitudinal axis. In some embodiments, the second member 114 may extend from the handle 108 at the first end portion 104 almost to the probe tip 112. The second member 114 may have an elongated, hollow structure and may be tubular. Second member 114 may be comprised of various materials including stainless steel, copper, Inconel, titanium, brass ceramic, or other materials.

Like the second member 114, the third member 116 may be have a hollow structure that extends along the longitudinal axis of first member 102, and it may be generally tubular. The third member 116 may be disposed outward, and may radially circumscribe the second member 114, along at least a portion of the extension of the second member 114. In some embodiments, the third member 116 may be in contact with and secured to the second member 114, for example, by brazing. A distal end 126 of the third member 116 may substantially enclose a portion of the second member 114, for example, by radially circumscribing the second member 114. Both the second member 114 and the third member 116 may have a distal end 128 and 126, respectively, forming a surface that is generally perpendicular to the longitudinal axis of the first member 102. As shown in FIG. 2, these distal ends 128 and 126 of the second member 114 and third member 116, respectively, may be coplanar with one another.

The third member 116 may comprise stainless steel, copper, ceramic, Inconel, titanium, brass, plastic or other materials.

Figure 3A:
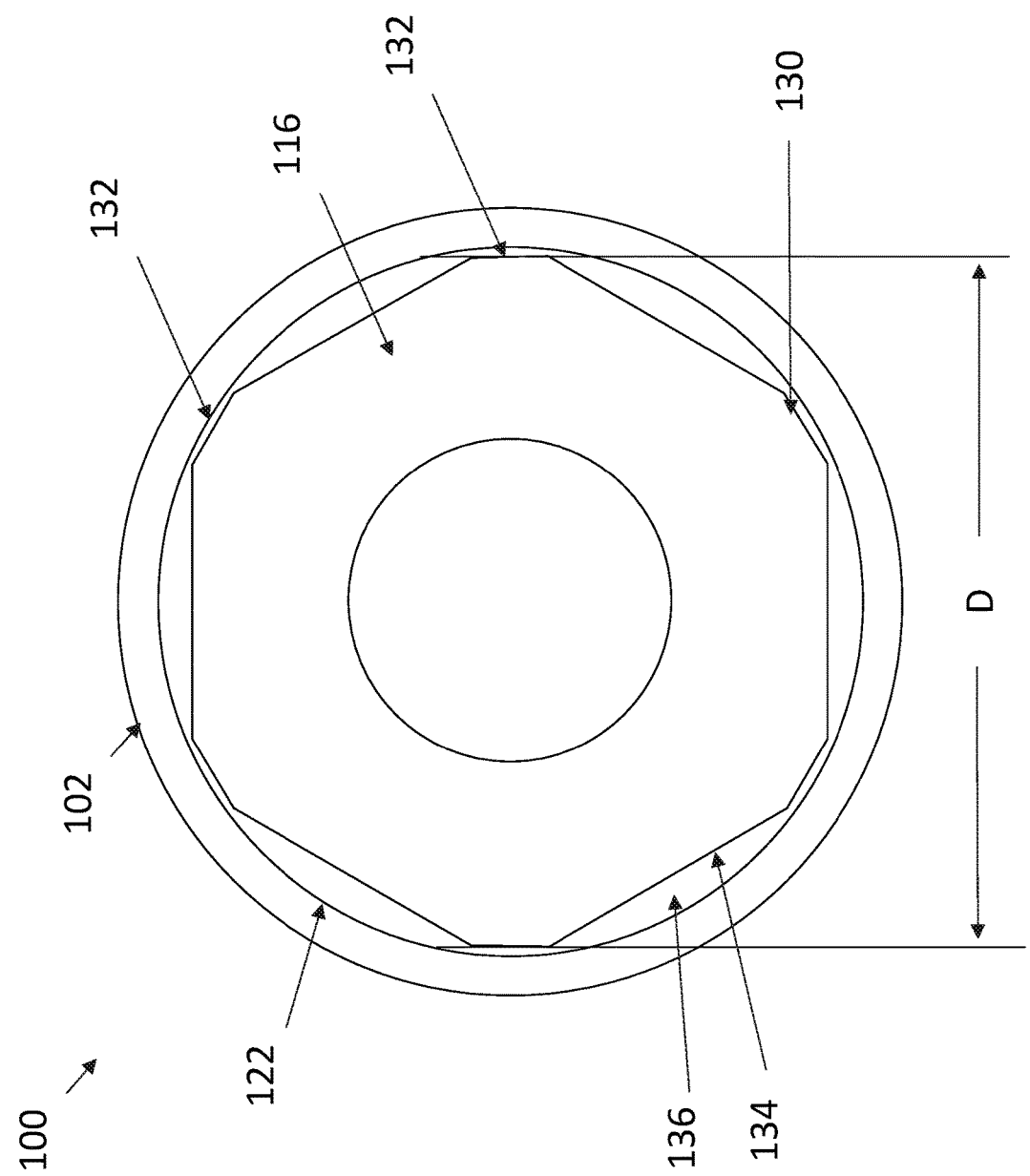
FIG. 3A is an end-view cross section of a probe in accordance with some embodiments.

FIG. 3A is an end-view cross section of a probe 100 in accordance with some embodiments, although this figure omits the second member 114. As illustrated, the third member 116 may have an outer surface 130 that engages the inner surface 122 of the first member 102 at one or more points 132. The third member 116 may be constructed such that it has an outer dimension 'D' that is sufficiently near to an inner dimension of the first member 102 such that the third member 116 is held in position with the first member 102. The outer surface 130 of the third member 116 may also have one or more sections 134 that have a dimension, measured across the longitudinal axis of the first member 102, that is less than the outer dimension 'D'. This section(s) 134, points of engagement 132, and the inner surface 122 of the first member 102 together define a passage 136 that may extend along a longitudinal length of the third member 116. This passage(s) 136 may be an annular passage. Section(s) 134 may be formed by machining the outer surface 130 of the third member 116.

In operation, a fluid may flow through the passage(s) 136 between the third member 116 and the first member 102 after having first passed through the second member 114 and a region near tip 112. This region may provide for the expansion of the fluid. By designing the passage(s) 136 with a small cross-sectional area, the bulk of the cooling fluid is closer to the inner surface 122 of the first member 102 than in designs (such as that referenced below) that use larger passages. Additionally, the velocity of the fluid in these passages is higher than in older designs in which the fluid passages have larger cross-sectional areas, such as that seen in U.S. Patent App. Pub. No. 2007/0149959, thereby reducing fluid boundary layer thickness and promoting heat transfer between the fluid and the first member 102 that is in thermal communication with surrounding tissue. Both of these features contribute to the improved thermal performance of the probes disclosed herein.

In some embodiments, some of the passages 136 may provide for an incoming fluid flow path from the proximal to the distal end of probe 100, replacing some or all of the function and use of the second member 114 as describe above. In some embodiments, some of the other passages 136 may provide for an outgoing fluid flow path from the distal to proximal ends of probe 100. In some embodiments, all of the passages 136 may be provide an inlet fluid flow path and second member 114 may provide the outlet fluid flow path.

Figure 3B:
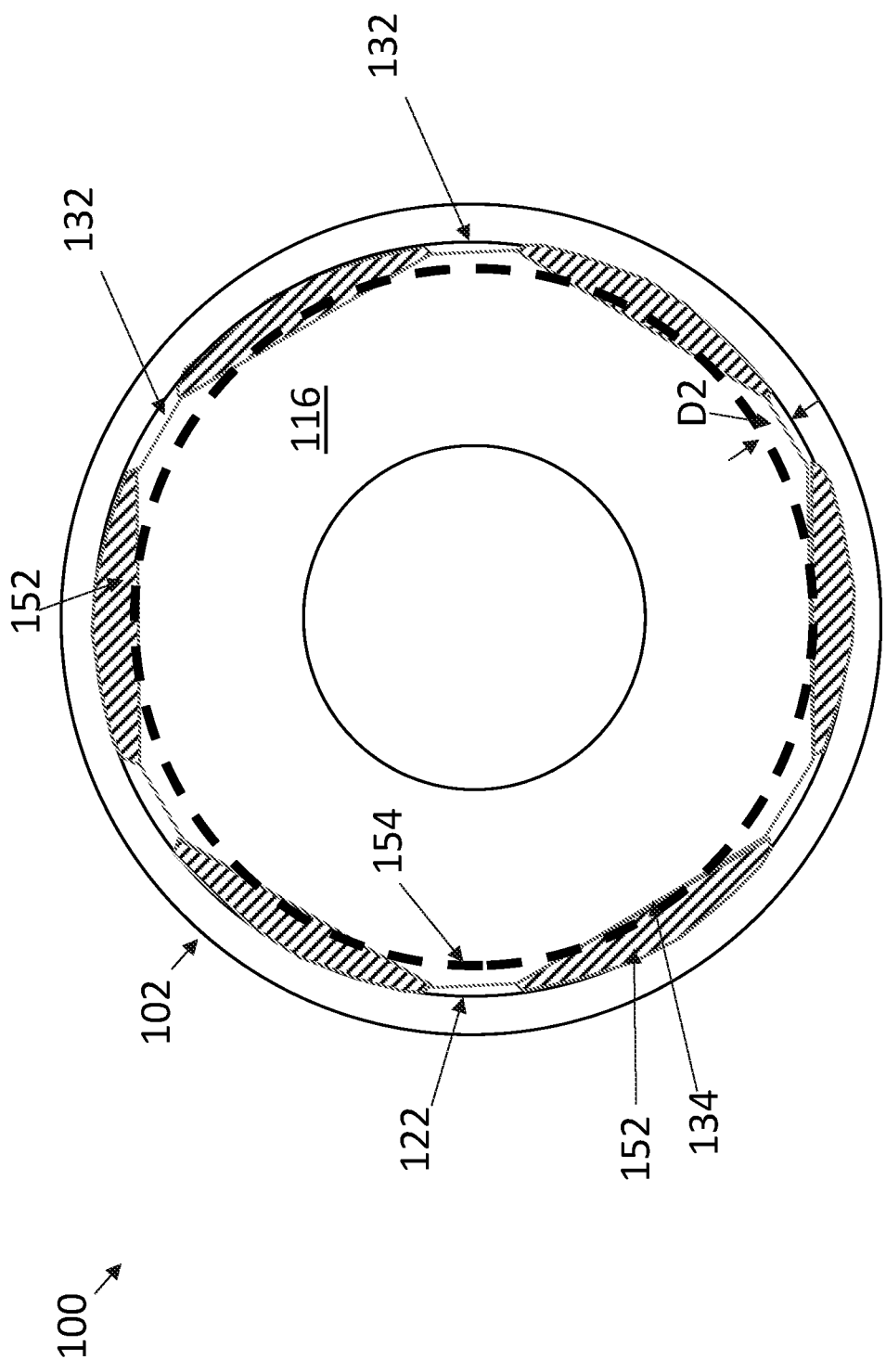
FIG. 3B another end view of the cross section of a probe of FIG. 3A in accordance with some embodiments.

The inventor has found that the location of the cross-sectional area of the passage(s) 136, relative to the inner surface 122 of the first member 102, has a significant effect on thermal performance. These cross-sectional area(s) of the passage(s) 136 are taken perpendicular to the longitudinal (major) axis of the first member 102. This relative positioning of the cross-sectional area 152 of the passage(s) 136, as seen in FIG. 3B, can be defined by the percentage of the cross-sectional area located between an inner surface 122 of the first member 102, and a boundary 154 located inwardly from the inner surface 122 of the first member 102. This boundary is inwardly offset from the inner surface 122 of the first member 102 by a distance 'D2' that is 10% of the largest inside cross sectional radius defined by the inner surface 122 of the first member 102. For example, in the case of a first member 102 having a circular inner cross section, the boundary is a circle that has a diameter that is 80% of the inside diameter of first member 102. Significant improvements in thermal performance have been observed when at least 70% of the total cross-sectional area of the passage(s) 136 is located in this region between the inner surface 122 of the first member 102 and this boundary. In some embodiments, at least 80% of the total cross-sectional area of the passage(s) 136 is located in this same region. In some embodiments, at least 90% of the total cross-sectional area of the passage(s) 136 is located in this region. In some embodiments, at least 100% of the total cross-sectional area of the passage(s) 136 is located in this region.

The inventor has also found that particular ratios of the cross-sectional area of the passage(s) 136 to the cross-sectional area of the first member 102 exhibit improvements in the thermal performance of probe 100. In these ratios, the inner surface 122 of the first member 102 defines the cross-sectional area within the first member 102. The total cross sectional flow area of the passage(s) 136, taken perpendicular to the longitudinal (major) axis of the first member 102, is defined by the engagement of the third member 116 with the first member 102. Ratios of the total cross-sectional flow area of the passage(s) 136 to the cross sectional area circumscribed within first member 102 by itself, having improved thermal performance include 0.05-0.3.

Figure 4:
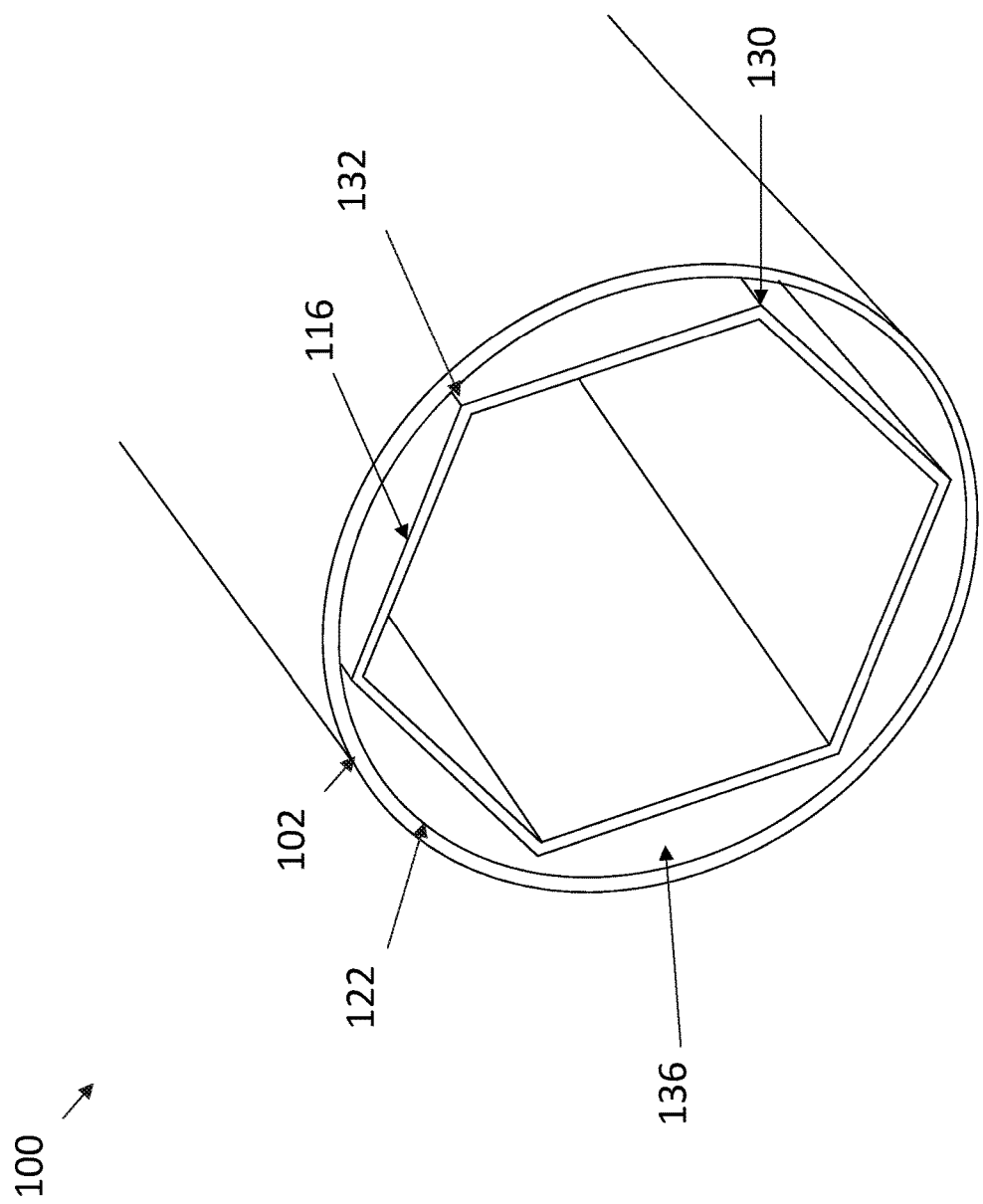
FIG. 4 is a perspective view of the cross-sectional area for fluid flow within a portion of a probe in accordance with some embodiments.

The cross-sectional profile of the third member 116 illustrated in FIG. 3A is a roughly hexagonal polygon having six locations of contact 132 between the third member 116 outer surface 130 and the inner surface 122 of the first member 102, together defining a total of six passages 136 for the flow of the fluid. This profile is but one example. Another example is illustrated in FIG. 4, a perspective view of the cross-sectional area for fluid flow within a portion of a probe 100 in accordance with some embodiments. This profile is largely similar to that provided in FIG. 3, however, the locations 132 at the outer surface 130 of the third member 116 that engage the inner surface 122 of the first member 102 have a reduced width, measured perpendicular to the longitudinal axis of the first member 102 and, roughly, around the circumference of the third member 116, such that the locations 132 are more akin to a point (or line when viewed along the length of third member 116) of contact rather than an area, giving third member 116 the six sides of a hexagon.

Figure 5:
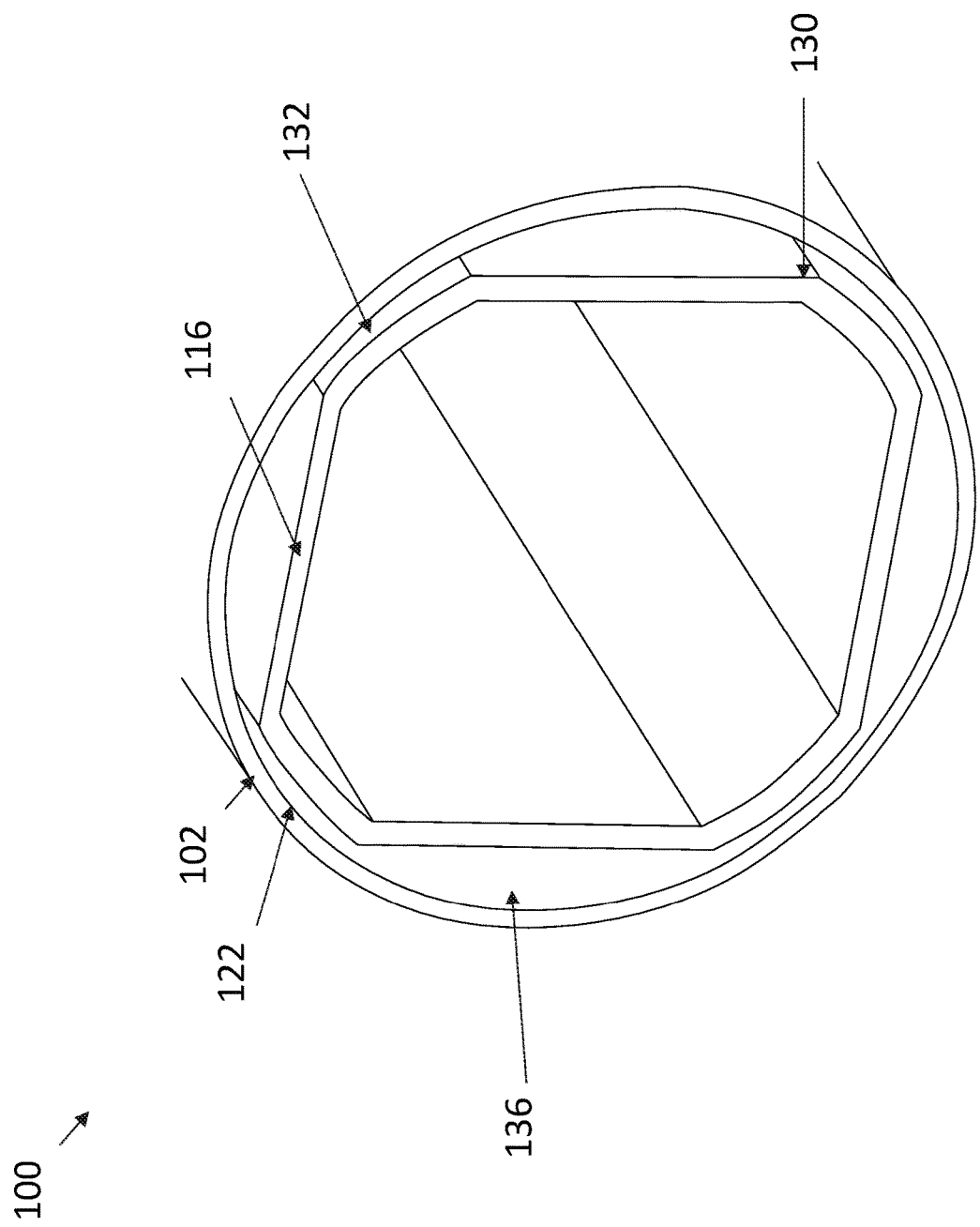
FIG. 5 is another perspective view of the cross-sectional area for fluid flow within a portion of a probe in accordance with some embodiments.

Another exemplary cross-sectional area for fluid flow is illustrated in FIG. 5. As shown, the engagement of third member 116 with the inner surface 122 of the first member 102 occurs in four locations 132, defining four passages 136. While this and earlier embodiments illustrate that the third member has a polygonal, or generally polygonal shape (which the expectation of possibly curved portions connecting the flat portions of the outer surface 130), the third member 116 is not limited to having a polygonal outer shape.

Likewise, the number of locations 132 at which the outer surface 130 of the third member 116 engages the inner surface 122 of the first member 102 can vary from as little as one (where that location may extend over an area around the circumference of the third member 116), to two, three, four, five, six, or even more. In turn, the number of locations 132 of engagement of the third member 116 and the first member 102 determines the number of passages between the two members.

A POSA will recognize that other shapes of the third member 116 may still result in the thermal improvements enabled by the features discussed herein.

The outer surface 130 of the third member 116 may have formed therein a plurality of channels 138 that direct the flow of fluid within, and sometimes between, the passages 136. These channels 138 may have various shapes, as illustrated in FIGS. 6A to 6D which are top-down views of the outer surface 130 of the third member 116 looking along the extension of the third member. As can be seen, these channels 138 may have a stepped shape, a series of alternating faces parallel and then perpendicular to the extension of third member 116 (FIG. 6A), a series of zig-zag shapes (FIG. 6B). In some embodiments, the shape may resemble zig-zag but using a series of continuously curving surfaces (FIG. 6C). In some embodiments, the channels 138 may spiral around the third member 116 along its extension (FIG. 6D). By alternating the direction of the fluid flow, channels 138 may cause a reduced boundary layer thickness of the fluid, thereby increasing the heat transfer coefficient. A POSA will recognize that other channel designs/patterns may be used to direct the flow of fluid within the passage(s) 136.

Figure 7:
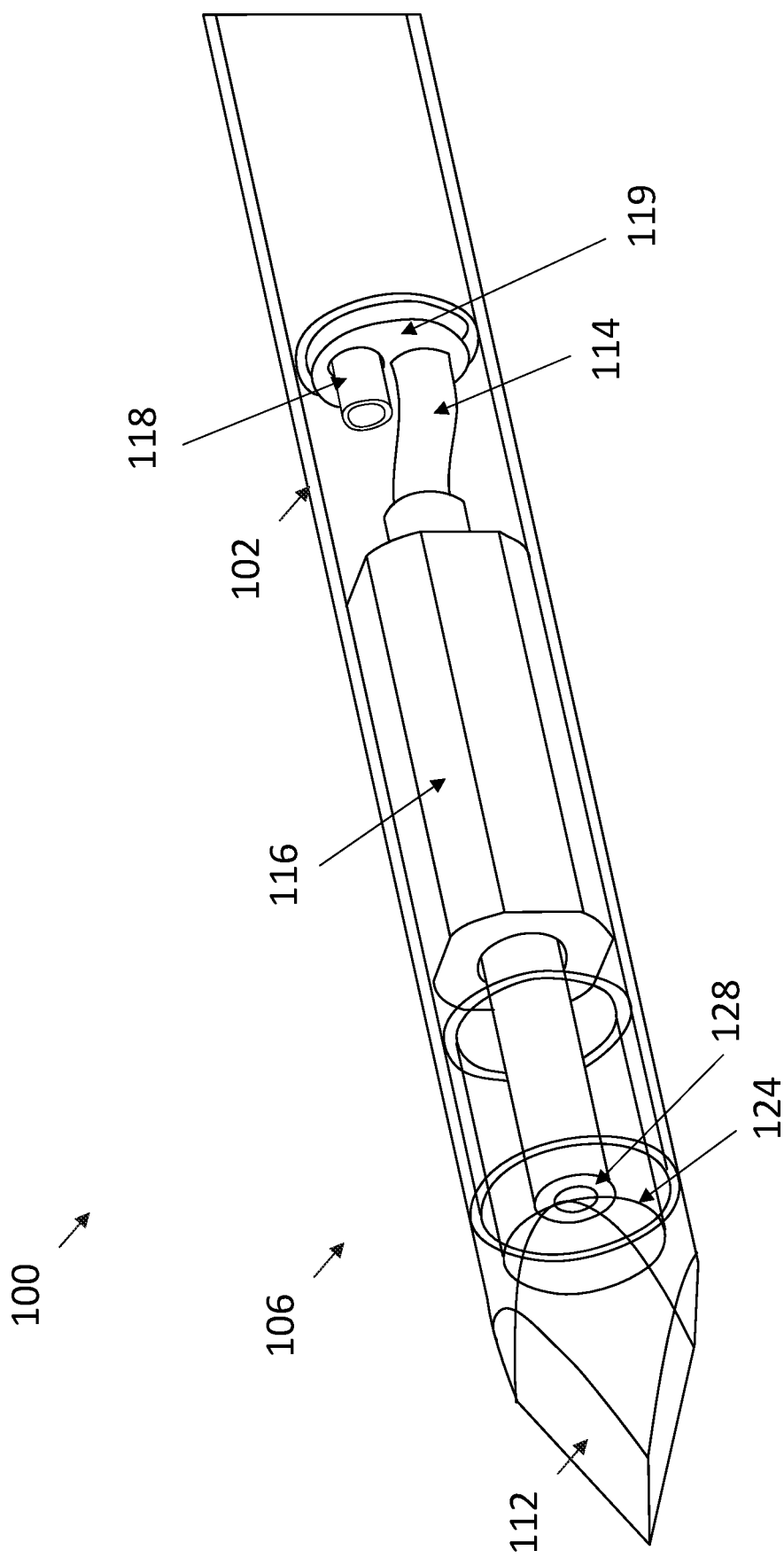
FIG. 7 is a perspective view of a portion of a probe in accordance with some embodiments.

Returning to FIG. 2, the third member 116 may have a proximal end 140 that may be located radially outward of and surround the second member 114, in embodiments in which the second member 114 extends through the length of the third member 116. A fourth member 118 is located between the handle 108 and the proximal end 140 of the third member 116. In some embodiments, fourth member 118 serves as a return line for the fluid after it has flowed through the passages 136. The fourth members 118 may be a double wall construction, with or without a vacuum or insulating material in between, and insulates the proximal end of 102 from the cold working fluid, serving as a termination point of the cooling portion of the first member 102. The fourth member 118 may be a hollow structure that extends within the first member 102. This structure may be tubular, and may comprise stainless steel, Inconel, titanium, ceramic, or other materials. As shown in FIG. 2, the fourth member 118 may be coaxial with and radially surround second member 114 (or other member that provides at least a portion of the flow path the fluid to the tip 112). In some embodiments, such as that illustrated in FIG. 7, a bulk head component 119, may be utilized to seal around and isolate inlet and outlet tubing, that may be of the second member 114 and fourth member 118, respectively. The inlet and outlet tubes may optionally be coaxial where they pass through the bulk head component 119. The region proximal to the bulk head component 119 may be insulated by physical insulation material, by vacuum, or both.

The fourth member 118 and a member providing at least a portion of the inlet flow path (which may be second member 114) may be surrounded by an insulating structure 142 between these members and first member 102. Insulating structure 142 serves to reduce the transfer of heat between tissue surrounding the first member 102 and fluid, thereby serving as a termination point of the working, cooling portion of the first member 102. Insulating structure 142 may comprise materials having low thermal conductivity, such as ceramics, and may utilize vacuum to aid in reducing heat transfer. This vacuum may be permanent, in that a vacuum is drawn in a sealed volume within structure 142, or it may be actively drawn during operating of the probe by a pump.

Figure 8A:
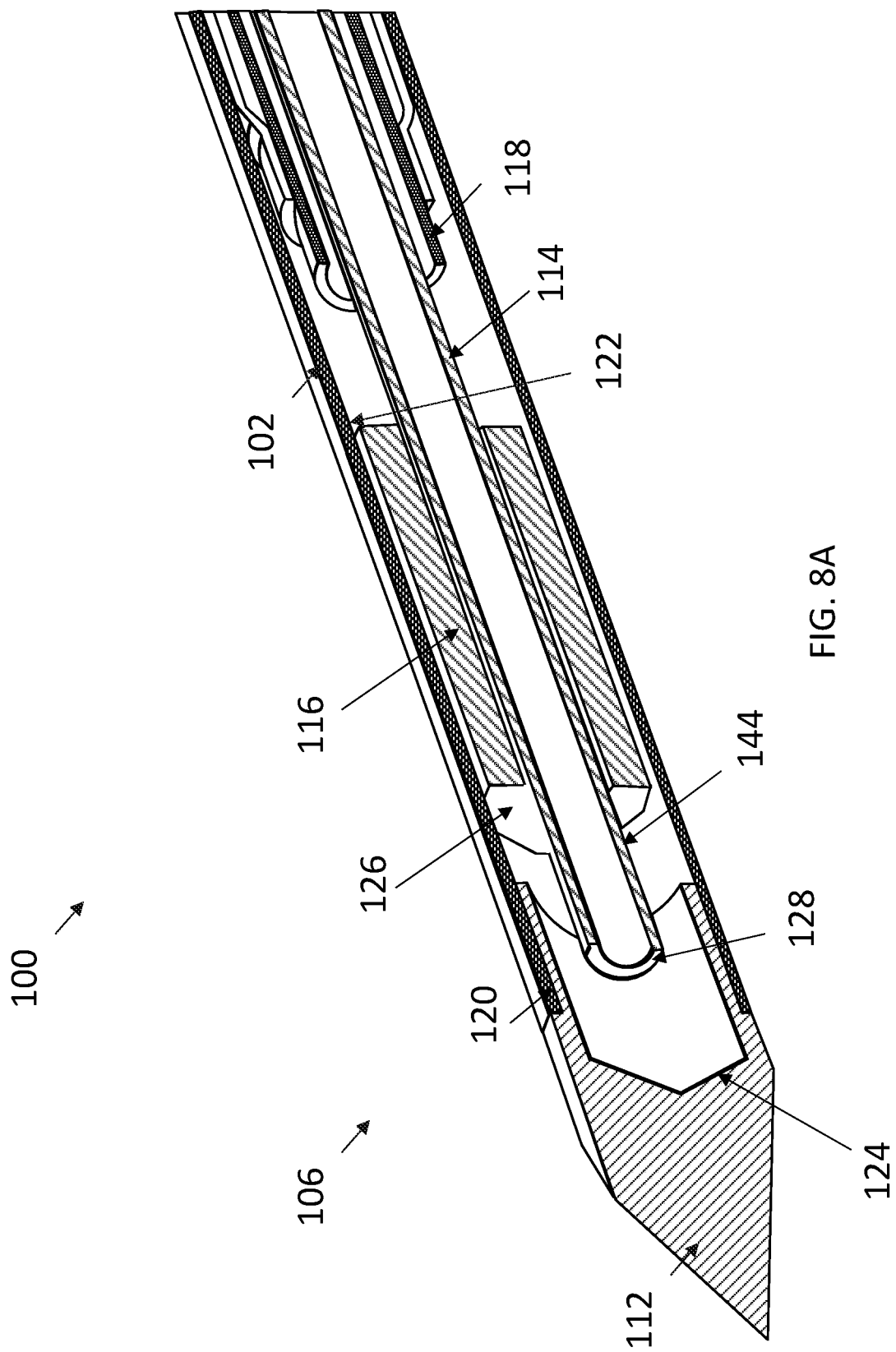
FIGS. 8A and 8B are perspective cross-sections of a portion of a probe in accordance with some embodiments.

Turning to FIG. 8A, illustrated is a probe 100 in which the second member 114 contains an extension 144 in accordance with some embodiments, otherwise the embodiment of FIG. 8A is largely similar to that of FIG. 2. Extension 144 serves to impinge the fluid upon the inner surface 124 of the tip 112. Additionally, extension 144 of second member 114 serves to reduce the cross-sectional flow areas closer to the tip 112. Both of these features may provide for improved heat transfer rates nearer the tip 112.

As can be seen in FIG. 8A, second members 114 and third members 116 are positioned within a first member 102 such that a distance measured between the distal end 128 of the extension 144 of the second member 114 and the tip 112 is less than a second distance measured between the distal end 126 of third member 116 and the tip 112. In some embodiments, the outer dimension 'D' of the third member 116 may be larger than an inner dimension between the tip 112 where the tip engages the first member 102. This larger dimension prevents the third member 116 from extending as far into the tip as the second member 114. Extension 144 has a sufficiently smaller outer dimension such that it can extend within the tip 112 to a location that is radially surrounded by both surface 120 and 122 of the tip 112 and the first member 102, respectively.

Figure 8B:
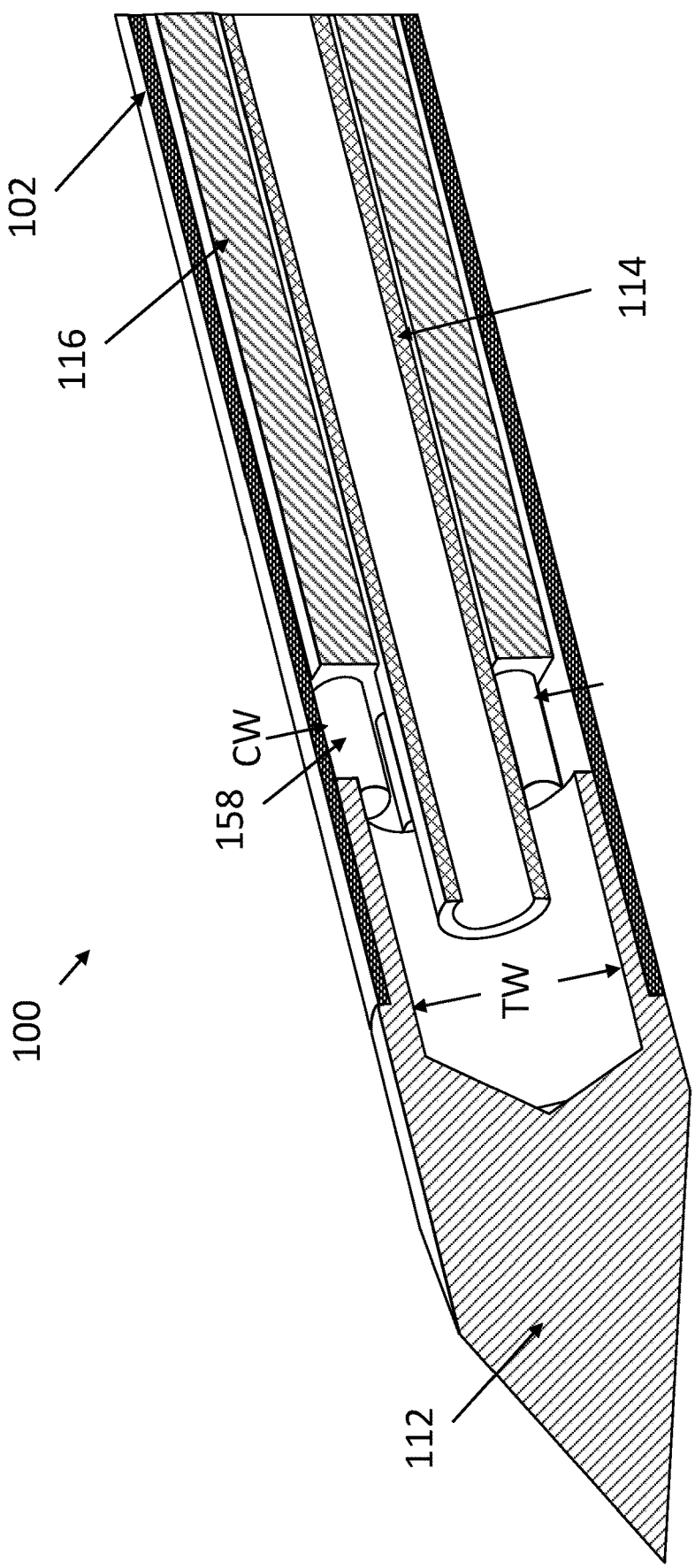

In some embodiments, such as that seen in FIG. 8B, distancing members 158, or projections, can be added to the distal face of third member 116, to prevent the third member 116 and the second member 114 from extending too far in the distal direction towards the tip 112. For example, distancing members 158 may have a combined width "CW" that is greater than the tip width "TW" of the tip 112 at its proximal end such that the distancing members 158 would engage a proximal surface of tip 112, thereby preventing the third member 116 and the second member 114 from extending too far in the distal direction towards the tip 112.

Figure 9:
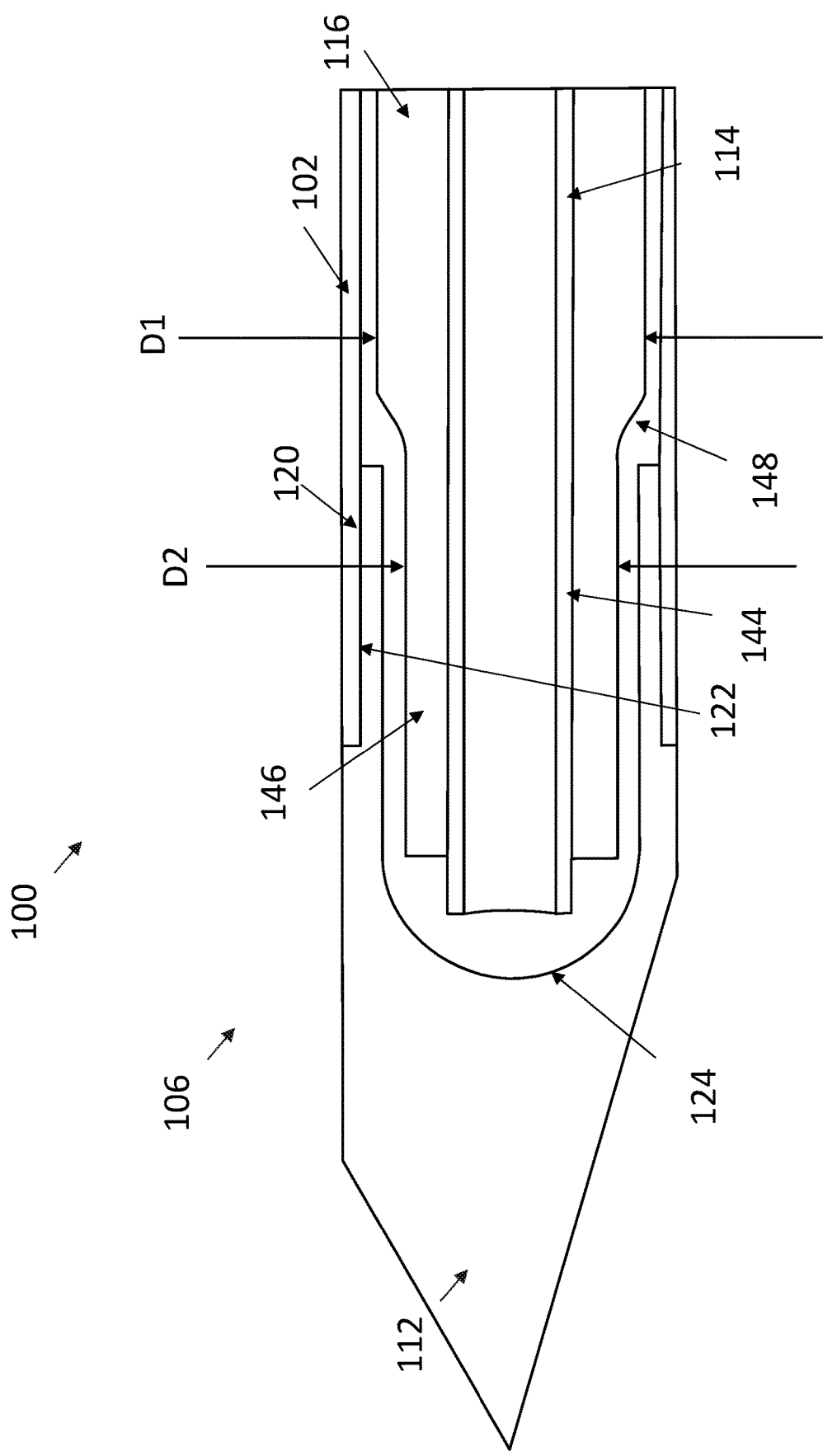
FIG. 9 is a cross-section of a tip of a probe in accordance with some embodiments.

An extension 146 may also be added to the third member 116 such that a portion of the third member 116 extends into a region within the tip 112 such that the extension 146 is radially surrounded by a portion of the tip 112, first member 102, or both. Such an embodiment is shown in the cross-section view of the tip 112 of probe 100 of FIG. 9. The third member 116 contains a first portion having an outer dimension 'D1' that is larger than an inner dimension of the tip 112, for example, between the surfaces 120 that engage first member 102. Third member 116 may also contain a second portion, extension 146, having an outer dimension "D2" which is less than the inner dimension of tip 112 at this same location. Extension 146 further reduces the cross-section flow area for the fluid, thereby increasing the heat transfer coefficient of the fluid in the region of the tip in the same manner as described above for the passages 136 between the third member 116 and the first member 102, and beyond that by merely providing an extended second member 114.

In some embodiments, the third member 116 may have a portion 148 between the larger first portion and the extended second portion. Portion 148 may be smooth. As used herein, 'smooth' describes a surface generally free of discontinuities (or "continuous"). Portion 148 may be smooth between its distal and proximal endpoints and be smooth or have a gradual transition between the first and second portions of the third member 116. This smooth transition provided by portion 148 reduces resistance to the flow of fluid within probe 100.

Figure 10:
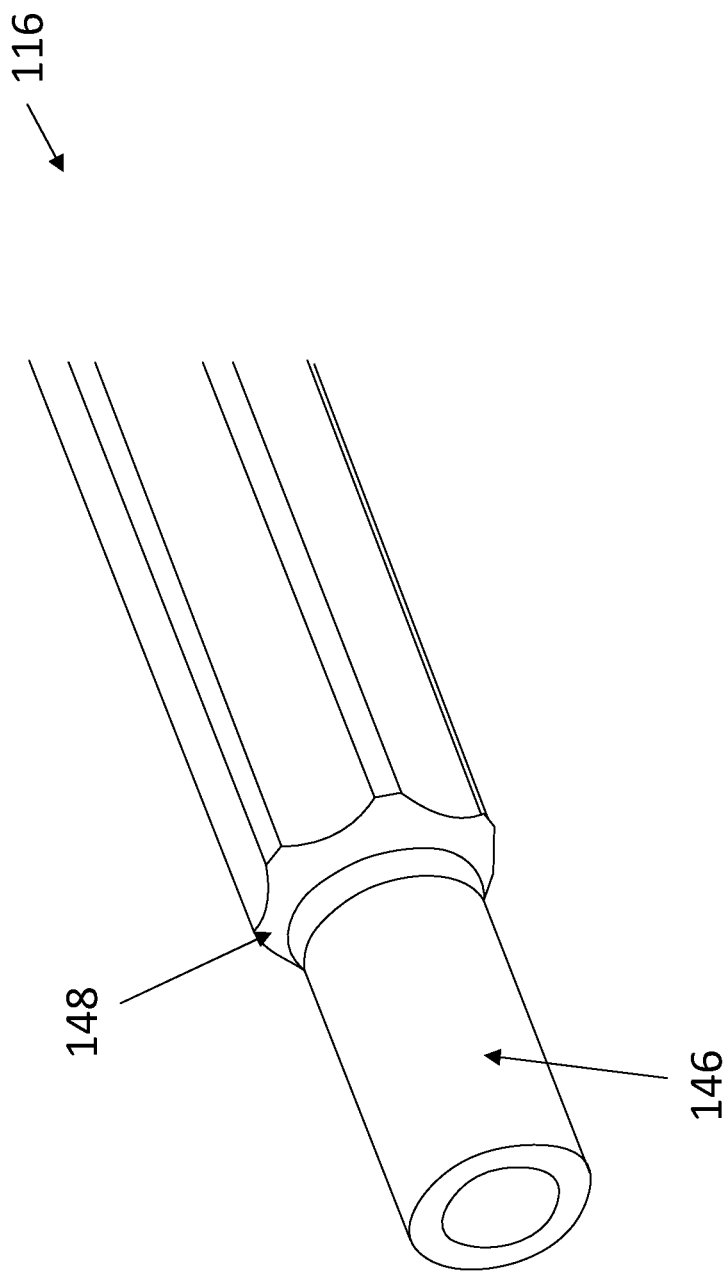
FIG. 10 is a perspective view of a component of a probe in accordance with some embodiments.

FIG. 10 is a perspective view of a third member 116 having an extension and a portion 148.

Figure 11A:
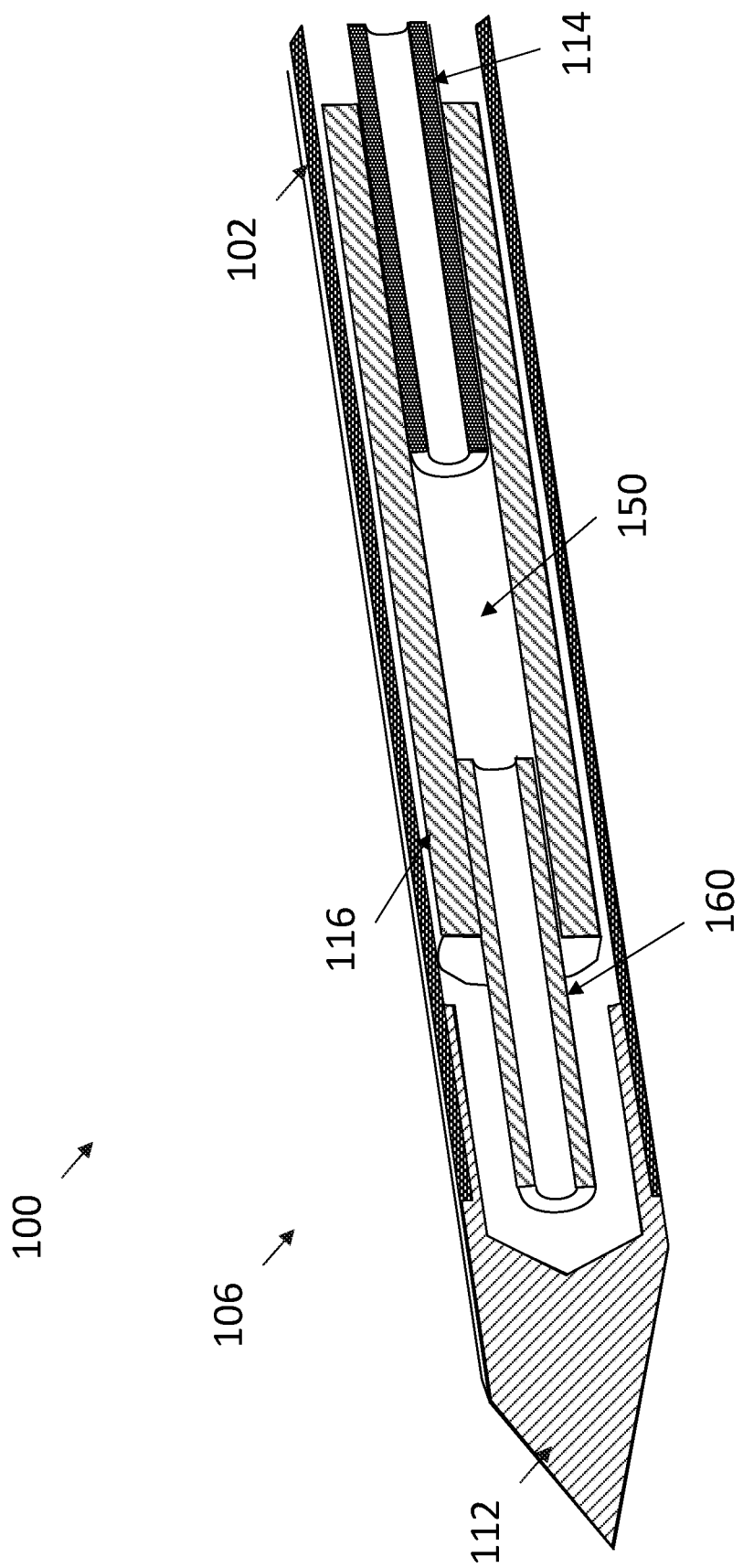
FIGS. 11A and 11B are other perspective, cross section views of a probe in accordance with some embodiments.

In accordance with some embodiments, a probe 100 having a fifth member 160 adjacent to the tip 112 as illustrated in FIG. 11A. Since fifth member 160 does not extend along the entire length of the third member 116, a section 150 of the third member 116 provides at least a portion of the incoming fluid flow path upstream of the fifth member 160. Second member 114 may extend along the longitudinal axis of the first member 102 near the proximal end of third member 116, and may engage third member 116 to provide a portion of the inlet fluid flow path.

Figure 11B:
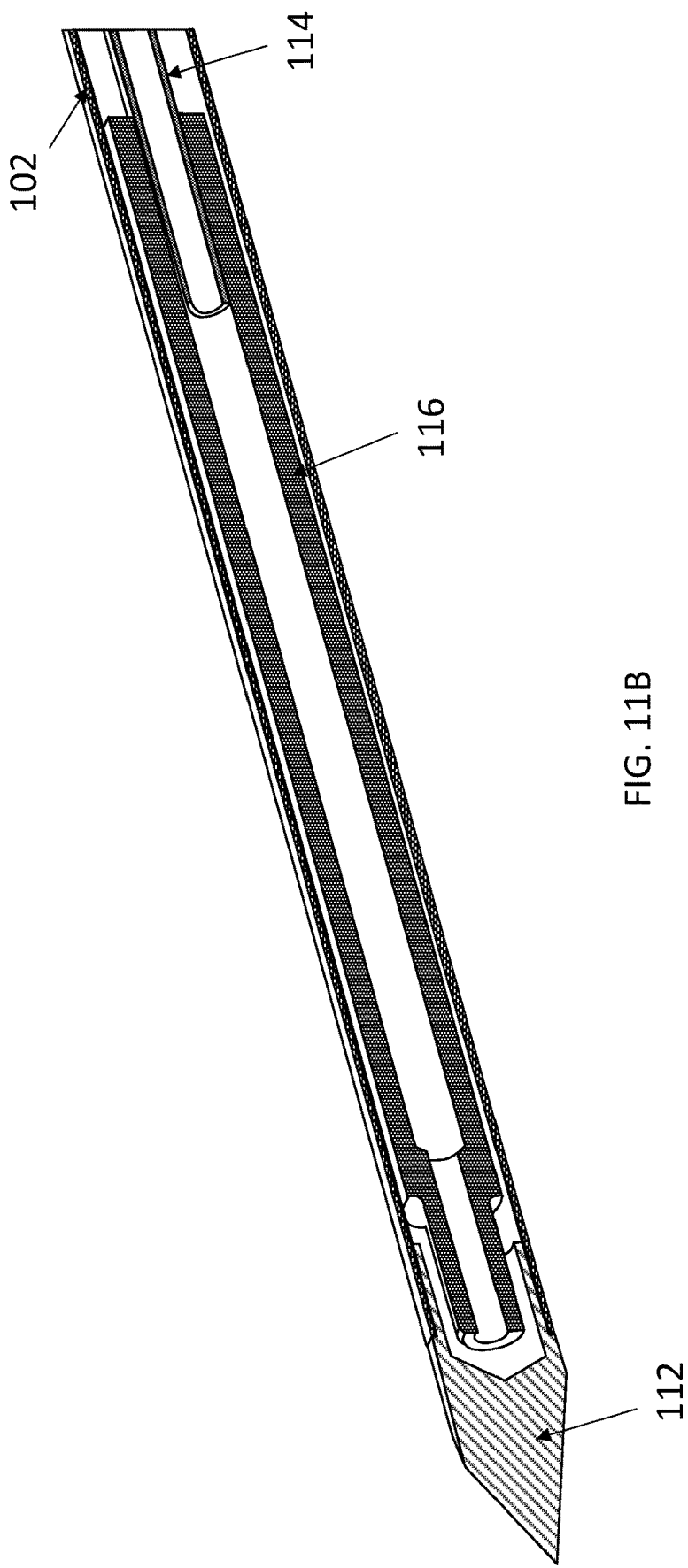

In some embodiments, the third member 116 may comprise the fifth member 160 in a unitary component, as illustrated in FIG. 11B. Third member 116 may still engage second member 114 at its proximal end. Manufacturing a unitary third member 116/fifth member 160 component providing for the function of both the third member 116 and the fifth member 160 may simplify assembly by reducing the number of components that may need to be connected to one another.

Figure 12:
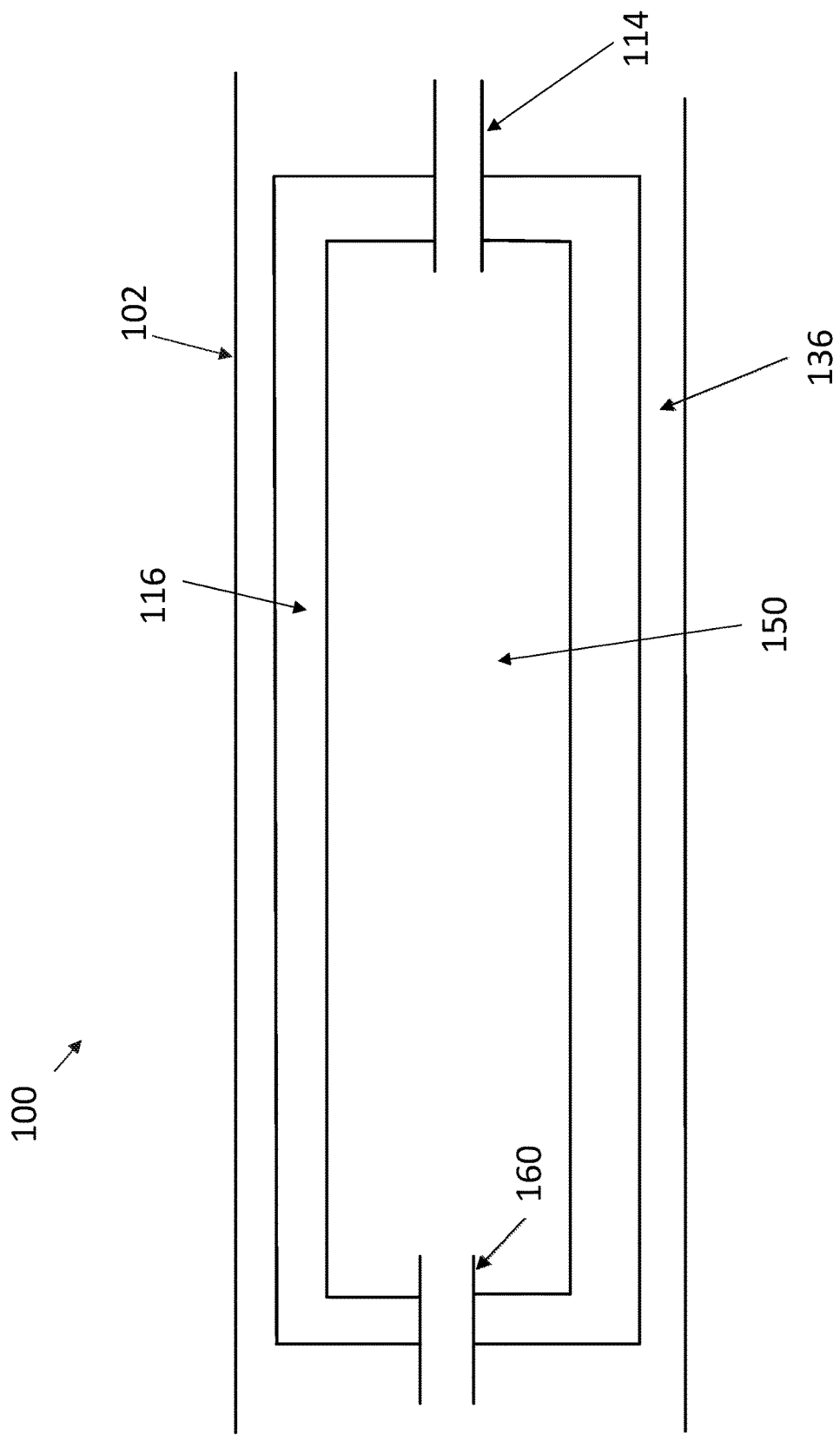
FIG. 12 is another perspective, cross section view of a probe in accordance with some embodiments.

As shown in FIG. 12, the second member 114 may be surrounded by the third member 116 at the proximal end of the third member 116, and the second member 114 may provide the fluid flow path into the section 150 of the third member 116. This arrangement provides for a greater ability to exchange heat between incoming fluid in section 150 and fluid flowing in the passages 136 between the third member 116 and the first member 102. This internal heat transfer between the fluid allows for more consistent temperatures along the length of the probe 100. As illustrated, member 116 may have a first inner dimension at its distal and proximal ends at which it engages fifth member 160 and second member 114, respectfully, and a second inner dimension between its distal and proximate ends. This second inner dimension allows the fluid to flow closer to the passages 136, and provides for a reduced radial thickness of the third member 116 in the section 150 when compared to its distal and proximal ends.

Figure 13:
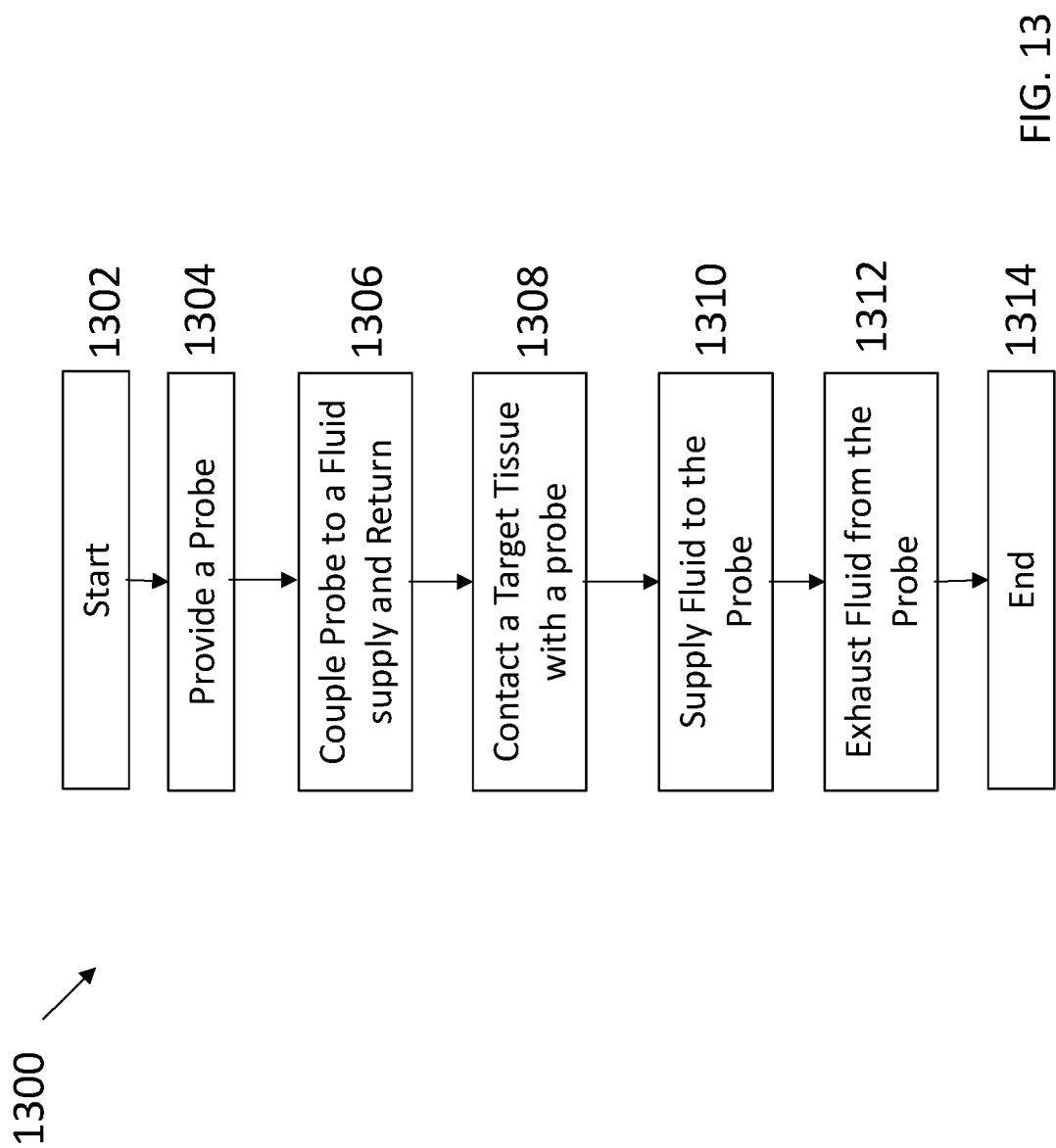
FIG. 13 is a block diagram of method of using a probe designed in accordance with some embodiments.

FIG. 13 is a block diagram of method 1300 of using a probe designed in accordance with some embodiments. The method starts at block 1302. At block 1304, a probe designed in accordance with one or more of the embodiments provided herein is provided. This probe is then coupled to a fluid supply and a fluid return at block 1306. At block 1308, the probe is positioned such that it is in contact with a target issue. Fluid is then supplied to the probe at block 1310, and then exhausted from the probe to the fluid return at block 1312. The method may end at block 1314. A POSA will recognize that other, conventional methods and procedures for running fluid to and from a probe may be utilized with probe 100 as described in the embodiments herein.

The improvements to the internal design of a cryoprobe which utilizes an internal fluid (liquid, gas, mixed, or other phase) as the cooling medium disclosed herein improves the cooling performance of the probe. These improvements increase the heat transfer rate between the outer surface of the probe and the internal working fluid. This increased heat transfer rate can be used to either cool/freeze tissue more quickly, freeze larger regions of tissue, consume less fluid or energy for the same amount of cooling or freezing performance, provide for a more uniform temperature along the probe, or a combination of any of the aforementioned advantages.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A probe, comprising:
a first member forming an outer surface of a cryoprobe;
a second member extending longitudinally within the first member; and
a third member disposed radially outward from the second member and extending along at least a portion of the second member, wherein the third member comprises a substantially continuous cross-sectional profile along its length and is configured to operably engage an inner surface of the first member to define at least one passage between the third member and the first member;
wherein the probe defines a fluid flow path for flow in a first direction through the second member and flow in a second direction opposite to the first direction through the at least one passage.

2. The probe of claim 1, wherein the cross-sectional profile of the third member comprises a polygonal shape.

3. The probe of claim 1, wherein the cross-sectional profile of the third member comprises a hexagonal polygon.

4. The probe of claim 1, further comprising a tip coupled to the first member.

5. The probe of claim 1, wherein a distal end of the second member is aligned with a distal end of the third member.

6. The probe of claim 1, wherein a distal end of the second member is longitudinally offset from a distal end of the third member.

7. The probe of claim 1, wherein the second and third members comprise different materials.

8. The probe of claim 1, wherein the third member is configured to operably engage the inner surface of the first member in at least two locations.

9. The probe of claim 1, wherein at least 70 percent of a cross-sectional area of the at least one passage defined between the third member and the first member is outward of a boundary, the boundary inwardly offset from an inner surface of the first member by a distance equal to 10 percent of the largest inner radius of the first member.

10. The probe of claim 1, wherein the first direction corresponds to a supply flow direction and the second direction corresponds to return flow direction.

11. The probe of claim 1, further comprising an insulating member positioned around the second member.

12. A method comprising:
providing the probe of claim 1;
providing fluid to the probe from a fluid supply; and
exhausting fluid from the probe.

13. The method of claim 12, wherein the providing fluid to the probe is performed by providing the fluid to the second member.

14. The method of claim 12, wherein the exhausting fluid from the probe comprises exhausting fluid in the second direction from the at least one passage.

15. The method of claim 12, wherein the cross-sectional profile of the third member comprises a hexagonal polygon.

16. The method of claim 12, wherein a distal end of the second member is aligned with a distal end of the third member.

17. The method of claim 12, wherein a distal end of the second member is longitudinally offset from a distal end of the third member.

18. A system, comprising:
a fluid supply;
a probe comprising;
a first member forming an outer surface of a cryoprobe;
a second member extending longitudinally within the first member; and
a third member disposed radially outward from the second member and extending along at least a portion of the second member, wherein the third member comprises a substantially continuous cross-sectional profile along its length and is configured to operably engage an inner surface of the first member to define at least one passage between the third member and the first member;
wherein the probe defines a fluid flow path for flow in a first direction through the second member and flow in a second direction opposite to the first direction through the at least one passage, the fluid flow path fluidly coupled to the fluid supply.

19. The system of claim 18, wherein the fluid supply is coupled to second member.

20. The system of claim 19, further comprising a fluid return, the fluid return coupled to the at least one passage.

* * * * *